United States Patent [19]

Isganitis et al.

[11] Patent Number: 6,042,640
[45] Date of Patent: Mar. 28, 2000

[54] DEODORIZATION OF SULFUR-CONTAINING SOLVENTS BY OXIDATION

[75] Inventors: Louis V. Isganitis, Rochester; Thomas W. Smith, Penfield, both of N.Y.

[73] Assignee: Xerox Corporation, Stamford, Conn.

[21] Appl. No.: 09/106,379

[22] Filed: Jun. 29, 1998

[51] Int. Cl.[7] .............................. C09D 11/02; C02F 1/72; C02F 1/76
[52] U.S. Cl. ..................... 106/31.02; 106/31.32; 106/31.58; 106/31.64; 106/31.87; 210/754; 210/758; 210/759
[58] Field of Search .............................. 106/31.02, 31.32, 106/31.64, 31.58, 31.87; 210/754, 758, 759

[56] References Cited

U.S. PATENT DOCUMENTS

| | | | |
|---|---|---|---|
| 3,867,509 | 2/1975 | Geiger et al. | 210/754 |
| 3,963,611 | 6/1976 | Dardenne-Ankringa, Jr. | 210/758 |
| 4,077,879 | 3/1978 | Smeck | 210/754 |
| 4,263,136 | 4/1981 | Gagliardi et al. | 210/759 |
| 5,096,589 | 3/1992 | Blind et al. | 210/754 |
| 5,171,441 | 12/1992 | Mason | 210/754 |
| 5,269,944 | 12/1993 | Kerollis et al. | 210/758 |
| 5,861,096 | 1/1999 | Mason et al. | 210/754 |

FOREIGN PATENT DOCUMENTS

| | | | |
|---|---|---|---|
| 57-18767 | 1/1982 | Japan . | |
| 4-103673 | 4/1992 | Japan . | |
| 4-103674 | 4/1992 | Japan | 106/31.02 |

OTHER PUBLICATIONS

Derwent abstract of JP04/103673, Apr. 1992.
Derwent abstract of JP04/103674, Apr. 1992.
Derwent abstract of JP57/018767, Jan. 1982.

*Primary Examiner*—Helene Klemanski
*Attorney, Agent, or Firm*—Judith L. Byorick

[57] ABSTRACT

Disclosed is a process which comprises contacting a sulfur-containing solvent with an oxidizing agent, said sulfur-containing solvent containing odor-causing impurities, thereby reducing odor. Another embodiment of the present invention is directed to a process for preparing an ink composition which comprises: (a) contacting a sulfur-containing solvent with an oxidizing agent, said sulfur-containing solvent containing odor-causing impurities, thereby reducing odor; and (b) admixing the sulfur-containing solvent with water and a colorant, thereby forming an ink composition.

24 Claims, No Drawings

DEODORIZATION OF SULFUR-CONTAINING SOLVENTS BY OXIDATION

BACKGROUND OF THE INVENTION

The present invention is directed to a method for deodorizing sulfur-containing solvents and to ink compositions containing the deodorized solvent. More specifically, the present invention is directed to a process for deodorizing sulfur-containing solvents with an oxidizing agent to convert odor-causing impurities therein to compounds with reduced or no objectionable odor. One embodiment of the present invention is directed to a process which comprises contacting a sulfur-containing solvent with an oxidizing agent, said sulfur-containing solvent containing odor-causing impurities, thereby reducing odor. Another embodiment of the present invention is directed to a process for preparing an ink composition which comprises: (a) contacting a sulfur-containing solvent with on oxidizing agent, said sulfur-containing solvent containing odor-causing impurities, thereby reducing odor; and (b) admixing the sulfur-containing solvent with water and a colorant, thereby forming an ink composition.

Ink jet printing systems generally are of two types: continuous stream and drop-on-demand. In continuous stream ink jet systems, ink is emitted in a continuous stream under pressure through at least one orifice or nozzle. The stream is perturbed, causing it to break up into droplets at a fixed distance from the orifice. At the break-up point, the droplets are charged in accordance with digital data signals and passed through an electrostatic field which adjusts the trajectory of each droplet in order to direct it to a gutter for recirculation or a specific location on a recording medium. In drop-on-demand systems, a droplet is expelled from an orifice directly to a position on a recording medium in accordance with digital data signals. A droplet is not formed or expelled unless it is to be placed on the recording medium.

Since drop-on-demand systems require no ink recovery, charging, or deflection, the system is much simpler than the continuous stream type. There are two types of drop-on-demand ink jet systems. One type of drop-on-demand system has as its major components an ink filled channel or passageway having a nozzle on one end and a piezoelectric transducer near the other end to produce pressure pulses. The relatively large size of the transducer prevents close spacing of the nozzles, and physical limitations of the transducer result in low ink drop velocity. Low drop velocity seriously diminishes tolerances for drop velocity variation and directionality, thus impacting the system's ability to produce high quality copies. Drop-on-demand systems which use piezoelectric devices to expel the droplets also suffer the disadvantage of a slow printing speed.

The other type of drop-on-demand system is known as thermal ink jet, or bubble jet, and produces high velocity droplets and allows very close spacing of nozzles. The major components of this type of drop-on-demand system are an ink filled channel having a nozzle on one end and a heat generating resistor near the nozzle. Printing signals representing digital information originate an electric current pulse in a resistive layer within each ink passageway near the orifice or nozzle, causing the ink in the immediate vicinity to evaporate almost instantaneously and create a bubble. The ink at the orifice is forced out as a propelled droplet as the bubble expands. When the hydrodynamic motion of the ink stops, the process is ready to start all over again. With the introduction of a droplet ejection system based upon thermally generated bubbles, commonly referred to as the "bubble jet" system, the drop-on-demand ink jet printers provide simpler, lower cost devices than their continuous stream counterparts, and yet have substantially the same high speed printing capability.

The operating sequence of the bubble jet system begins with a current pulse through the resistive layer in the ink filled channel, the resistive layer being in close proximity to the orifice or nozzle for that channel. Heat is transferred from the resistor to the ink. The ink becomes superheated far above its normal boiling point, and for water based ink, finally reaches the critical temperature for bubble formation or nucleation of around 280° C. Once nucleated, the bubble or water vapor thermally isolates the ink from the heater and no further heat can be applied to the ink. This bubble expands until all the heat stored in the ink in excess of the normal boiling point diffuses away or is used to convert liquid to vapor, which removes heat due to heat of vaporization. The expansion of the bubble forces a droplet of ink out of the nozzle, and once the excess heat is removed, the bubble collapses on the resistor. At this point, the resistor is no longer being heated because the current pulse has passed and, concurrently with the bubble collapse, the droplet is propelled at a high rate of speed in a direction towards a recording medium. The resistive layer encounters a severe cavitational force by the collapse of the bubble, which tends to erode it. Subsequently, the ink channel refills by capillary action. This entire bubble formation and collapse sequence occurs in about 10 microseconds. The channel can be refired after 100 to 500 microseconds minimum dwell time to enable the channel to be refilled and to enable the dynamic refilling factors to become somewhat dampened. Thermal ink jet processes are well known and are described in, for example, U.S. Pat. No. 4,601,777, U.S. Pat. No. 4,251,824, U.S. Pat. No. 4,410,899, U.S. Pat. No. 4,412,224, and U.S. Pat. No. 4,532,530, the disclosures of each of which are totally incorporated herein by reference.

Japanese Patent Publication JP-4103673, the disclosure of which is totally incorporated herein by reference, discloses a water-based ink for ink jet recording containing water, an aqueous dye, and a water soluble organic solvent, further containing as a deodorizer a benzotriazole derivative compound of the formula

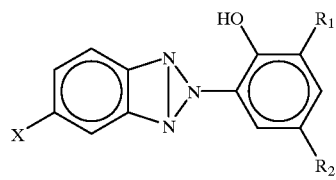

wherein each of $R_1$ and $R_2$ are hydrogen, hydroxy, or alkyl groups with 1 to 12 carbon atoms, and X is hydrogen or halogen. The deodorizer removes odor from organic solvents, such as glycol ethers and DMSO.

In some water miscible solvents desirable for use in aqueous ink jet inks, particularly those containing sulfur (such as sulfolane), very low concentrations of unoxidized sulfur-containing compounds can impart a very disagreeable odor to the solvent, even at the parts per million and parts per billion levels. Sulfolane is a polar, aprotic solvent that has found use in a wide variety of ink jet ink formulations. Its high boiling point makes it act as a humectant, and it also imparts some level of penetration to inks. For use in ink jet inks, this solvent must undergo extensive purification because of odor and, at times, color associated with impurities often found in the material. Even after extensive purification, certain impurities at the parts per billion level in the solvent can still result in significant odor. In addition, these impurities are less soluble in water than pure sulfolane, so that when the solvent is admixed with water to make the ink, the impurities have a greater tendency to vaporize, thereby accentuating the odor. Known purification methods include extensive distillation followed by passing the material through carbon bed filters, and the like; distillation alone is not sufficient to remove these impurities. These methods are expensive, take long periods of time, generate a substantial amount of waste, and do not enable uniform results; even after use of these purification methods, unacceptable odor can still remain. Other sulfur-containing solvents, such as alkyl sulfoxides or alkyl sulfones, can exhibit similar problems.

Accordingly, while known materials and methods are suitable for their intended purposes, a need remains for improved methods for deodorizing sulfur-containing solvents. In addition, a need remains for improved ink compositions suitable for use in thermal ink jet printers. Further, a need remains for methods for treating impurities in sulfur-containing solvents which enable reduction or elimination of undesirable odor from the treated material. Additionally, a need remains for methods for deodorizing sulfur-containing solvents which are cost effective. There is also a need for methods for deodorizing sulfur-containing solvents which can be employed prior to admixing the sulfur-containing solvents with other ink components. In addition, there is a need for methods for deodorizing sulfur-containing solvents which can be employed with an ink composition containing sulfur-containing solvents and other ink ingredients. Further, there is a need for methods for deodorizing sulfur-containing solvents which also disinfect the ink. Additionally, there is a need for methods for oxidizing common impurities in sulfur-containing solvents which cause an undesirable odor and/or, wherein the oxidized forms of the impurities exhibit little or no undesirable odor and/or color. A need also remains for ink compositions containing materials which, when incorporated into thermal ink jet ink compositions containing sulfur-containing solvents, oxidize impurities which cause an undesirable odor and/or color, thereby converting the impurities to a form having little or no undesirable odor and/or color, and which also impart to the ink composition antibacterial properties.

SUMMARY OF THE INVENTION

It is an object of the present invention to provide methods for treating compositions containing sulfur-containing solvents with the above noted advantages.

It is another object of the present invention to provide improved methods for treating impurities in sulfur-containing solvents.

It is yet another object of the present invention to provide improved ink compositions suitable for use in thermal ink jet printers.

It is still another object of the present invention to provide methods for treating impurities in compositions containing sulfur-containing solvents which enable reduction or elimination of undesirable odor from the treated material.

Another object of the present invention is to provide methods for treating impurities in sulfur-containing solvents which are cost effective.

Yet another object of the present invention is to provide methods for treating impurities in sulfur-containing solvents which can be employed prior to admixing the sulfur-containing solvents with other ink components.

Still another object of the present invention is to provide methods for treating impurities in sulfur-containing solvents which can be employed with an ink composition containing sulfur-containing solvents and other ink ingredients.

It is another object of the present invention to provide methods for treating impurities in sulfur-containing solvents which also disinfect the ink.

It is yet another object of the present invention to provide methods for oxidizing common impurities in sulfur-containing solvents which cause an undesirable odor and/or, wherein the oxidized forms of the impurities exhibit little or no undesirable odor and/or color.

It is still another object of the present invention to provide ink compositions containing materials which, when incorporated into inks containing sulfur-containing solvents, oxidize impurities which cause an undesirable odor and/or color, thereby converting the impurities to a form having little or no undesirable odor and/or color, and which also impart to the ink composition antibacterial properties.

These and other objects of the present invention (or specific embodiments thereof) can be achieved by providing a process which comprises contacting a sulfur-containing solvent with an oxidizing agent, said sulfur-containing solvent containing odor-causing impurities, thereby reducing odor. Another embodiment of the present invention is directed to a process for preparing an ink composition which comprises: (a) contacting a sulfur-containing solvent with an oxidizing agent, said sulfur-containing solvent containing odor-causing impurities, thereby reducing odor; and (b) admixing the sulfur-containing solvent with water and a colorant, thereby forming an ink composition.

DETAILED DESCRIPTION OF THE INVENTION

The present invention is directed to a process for converting odor-causing impurities in sulfur-containing solvents to forms which exhibit little or no undesirable odor and/or color. By "sulfur-containing solvents" is meant any material or mixture of materials which is liquid at 25° C. and 1 atmosphere of pressure and which contains molecules which include sulfoxide groups or sulfone groups. For example, sulfolane, of the formula

in its pure form is a solid at 25° C. and 1 atmosphere of pressure (m.p. 25–28° C.), but it is commonly used as a solvent because it is liquid when admixed with small amounts of other materials such as water (for example, a mixture of 97 percent by weight sulfolane and 3 percent by weight water is a liquid at 25° C. and 1 atmosphere of pressure. While not being limited to any particular theory, it is believed that the odor causing impurities generally are believed to be molecules which include or contain sulfide groups or mercaptan groups, although the present invention is not limited to the removal or alteration of such impurities. For example, sulfolane is frequently prepared by the reaction of butadiene with sulfur dioxide to form sulfolene, followed by hydrogenation in the presence of a catalyst, as follows:

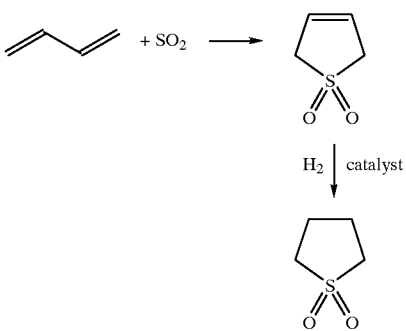

While not being limited to any particular theory, it is believed that odor-causing impurities which can be found in sulfolane include (but are not necessarily limited to) dibutyl disulfide, of the formula

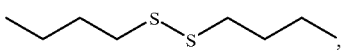

and tetrahydrothiophene, of the formula

Other examples of sulfur-containing solvents include substituted sulfolanes, such as 2,4-dimethylsulfolane, 3-methylsulfolane, sulfoxides, such as dimethyl sulfoxide, mixtures thereof with other liquids such as water, and the like.

The present invention is directed to a process which comprises contacting a sulfur-containing solvent containing odor-causing impurities with an oxidizing agent, thereby reducing odor. Again, while not being limited to any particular theory, it is believed that the oxidizing agent oxidizes the impurities to a form in which they exhibit little or no undesirable odor.

The oxidizing agent can be contacted with the sulfur-containing solvent and impurities by any desired or effective method. For example, the sulfur-containing solvent can be admixed with the oxidizing agent, either alone or in contained in a solution such as an aqueous solution, or the sulfur-containing solvent can be passed through a bed or column or filter cartridge containing either a solid oxidizing agent or a solid material such as carbon or the like onto the surface of which is adsorbed an oxidizing agent, or the like. Treatment of the sulfur-containing solvent by passing it through a column or bed or filter containing the oxidizing agent has the added benefit of keeping excess oxidant out of the treated sulfur-containing solvent, and thus out of an ink into which the sulfur-containing solvent may subsequently be included.

The oxidizing agent can be added either to the sulfur-containing solvent alone or to a mixture of the sulfur-containing solvent and one or more additional components. For example, a sulfur-containing solvent such as sulfolane can be subjected to oxidation by admixing the oxidizing agent with a mixture of water and sulfur-containing solvent, with water being present in the water/solvent mixture in an amount typically from about 5 to about 50 percent by weight, although the relative amounts can be outside of this range. When the sulfur-containing solvent is to be used in an ink formulation, it may be desired in some instances, depending on the desired relative amounts of ingredients in the ink, to dilute the solvent as little as possible. Many other ink ingredients, particularly colorants, are commercially supplied as fairly dilute water solutions, and if the ink is desired to contain a substantial amount of the sulfur-containing solvent, dilution of the solvent may make it difficult to achieve the concentrations desired for other ingredients in the ink. In addition, diluting the sulfur-containing solvent dilutes the impurities and the oxidant, thus slowing down the deodorizing reaction. Similarly, the oxidizing agent can be added to the sulfur-containing solvent either alone or as a component in a concentrated or dilute mixture. When the sulfur-containing solvent is to be used in an ink formulation, in some instances it may be desired to use the oxidizing agent in as concentrated a form as possible for reasons similar to those for desiring to keep the solvent as undiluted as possible.

The specific amount of oxidizing agent added to the sulfur-containing solvent is selected based on considerations such as the speed at which the oxidation reaction is desired to take place (with more oxidizing agent enabling faster reaction), the particular solvent selected, the particular oxidizing agent selected, and the estimated concentration of odor-causing impurities in the sulfur-containing solvent. When the sulfur-containing solvent is to be used as a component in an ink, subsequent to the oxidation of the impurities, excess oxidizing agent preferably is either removed from the mixture or converted to a nonreactive form by any desired method to prevent oxidation of other ink ingredients; accordingly, in this instance it can be desirable to use the minimum amount of oxidizing agent possible to obtain the desired results with respect to odor reduction and reaction speed. Typically, the ratio by weight of oxidizing agent to sulfur-containing solvent is from about $1 \times 10^{-5}:1$ to about $1 \times 10^{-2}:1$, although the relative amounts of oxidizing agent and sulfur-containing solvent can be outside of this range. Typically, the oxidant is added to the sulfur-containing solvent in an amount of from about 10 to 100 times the amount by weight of the impurities contained in the sulfur-containing solvent, although the amount can be outside of this range.

Optionally, the mixture of sulfur-containing solvent and oxidizing agent is heated to speed the oxidizing reaction and to convert excess oxidizing agent to a nonreactive form. Heating is particularly effective at removing or converting excess oxidizing agent when the selected oxidizing agent is chlorine dioxide or a peroxide such as hydrogen peroxide. The mixture of sulfur-containing solvent and oxidizing agent typically is heated to a temperature of from about 25 to about 150° C., and preferably from about 50 to about 100° C., although the temperature can be outside of these ranges. Heating is effected for any desired or effective period of time for removing the objectionable odor; typically heating takes place for a period of from about 1 to about 2 hours, although the time can be outside of this range. The heating time can range from minutes to several hours, depending on the half life of the oxidant at the reaction temperature. Oxidizing agents insoluble in the sulfur-containing solvent can be dissolved in water and the aqueous oxidizing solution can then be added to the sulfur-containing solvent, with the amount of water used being sufficient to maintain solubility of the oxidizing agent when admixed with the sulfur-containing solvent. Oxidizing agents insoluble in the sulfur-containing solvent are also particularly suitable for reaction methods which entail passing the sulfur-containing solvent through a bed, column, or filter of the oxidizing agent. For example, when the sulfur-containing solvent is sulfolane, insoluble oxidizing agents include sodium percarbonate, sodium peroxide, calcium peroxide, and the like.

One preferred oxidizing agent is chlorine dioxide. For example, a water solution containing chlorine dioxide in an amount of from about 0.01 percent by weight (100 parts per million) to about 5 percent by weight (50,000 parts per million), although the amount can be outside of these ranges, can be added to a sulfur-containing solvent, such as sulfolane. Commercial systems are available that generate chlorine dioxide solutions in water. Chlorine dioxide generally is soluble in water to a concentration of about 3,000 parts per million (0.3 percent by weight) at 25° C. and 1 atmosphere of pressure, but stabilized solutions can enable substantially higher concentrations. One example of a commercially available source of chlorine dioxide is a stabilized aqueous solution containing 5 percent by weight chlorine dioxide, 3.65 percent by weight buffering agents (sodium carbonates $Na_2CO_3$ and $NaHCO_3$), and 91.35 percent by weight water, available from International Dioxcide, Inc., Clark, N.J., under the names Anthium Dioxcide, Anthium 200 (containing 2 percent by weight chlorine dioxide in water), Carnebon 200 (containing 2 percent by weight chlorine dioxide in water), and Endimal C. Chlorine dioxide can also be generated by the reaction of liquid sodium chlorite and hydrochloric acid in apparatus such as that available from Vulcan Chemical Technologies, Inc. (Compu-Klor$_2$), West Sacramento, Calif. In one embodiment, the 5 percent solution is diluted with water by from about 1:50 to about 1:100 to obtain an aqueous solution of the desired concentration. The chlorine dioxide can be admixed with the sulfur-containing solvent (such as sulfolane) in any desired or effective amount. Optionally, the oxidation reaction between the impurities and the chlorine dioxide can be activated by the addition of an activator instead of or in addition to heating. Examples of suitable activators include hydrochloric acid and the like.

Additional suitable oxidizing agents include peroxides, such as hydrogen peroxide, alkali metal peroxides, such as sodium peroxide and the like, alkaline earth metal peroxides, such as calcium peroxide and the like, alkylhydroperoxides, of the general formula

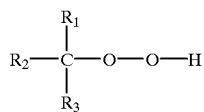

wherein $R_1$, $R_2$, and $R_3$ each, independently of the others, are alkyl groups, preferably with 1 or 2 carbon atoms, although the number of carbon atoms can be outside of this range, or alkylaryl groups, preferably with from 7 to about 9 carbon atoms, although the number of carbon atoms can be outside of this range, such as t-butyl hydroperoxide, cumene hydroperoxide, and the like, dialkyl peroxides, of the general formula

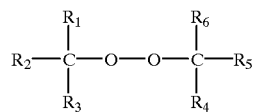

wherein $R_1$, $R_2$, $R_3$, $R_4$, $R_5$, and $R_6$ each, independently of the others, are alkyl groups, preferably with 1 or 2 carbon atoms, although the number of carbon atoms can be outside of this range, or alkylaryl groups, preferably with from 7 to about 9 carbon atoms, although the number of carbon atoms can be outside of this range, such as di-t-butyl peroxide, di-cumyl peroxide, and the like, wherein the class of dialkyl peroxides also includes substituted dialkyl peroxides, such as t-butylperoxybenzoate, of the formula

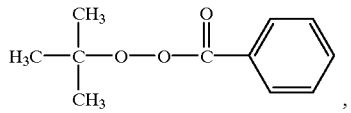

t-butylperoxy isopropyl carbonate, of the formula

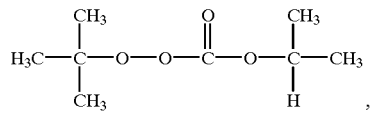

and the like, acyl peroxides, of the general formula

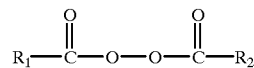

wherein $R_1$ and $R_2$ are each, independently of the others, alkyl groups, preferably with 1 or 2 carbon atoms, aryl groups, preferably with from 6 to about 9 carbon atoms, or alkylaryl groups, preferably with from 7 to about 9 carbon atoms, such as benzoyl peroxide, pivaloyl peroxide, and the like, peroxydisulfates, such as sodium peroxydisulfate, potassium peroxydisulfate, ammonium peroxydisulfate, and the like, peroxyborates, such as sodium perborate monohydrate, sodium perborate tetrahydrate, and the like, percarbonates, such as sodium percarbonate and the like, and the like, as well as mixtures thereof. Peroxides such as the above are available from, for example, Aldrich Chemical Co., Milwaukee, Wis., and Alfa Aesar, division of Johnson Matthey Catalog Co., Inc., Ward Hill, Mass. Preferred oxidizing agents have oxidation potentials greater than those typical of dialkylsulfides, preferably from about 1.4 to about 1.6 volts versus the standard Calomel electrode, and are preferably not so strongly oxidizing that the oxidation reaction cannot be limited to the oxidation of sulfide or mercaptan groups to sulfoxides or sulfones.

When the sulfur-containing solvent is intended for use in an ink composition, preferably the sulfur-containing solvent is admixed with the oxidizing agent prior to admixing the sulfur-containing solvent with the other ink ingredients, although this process is not required.

Ink compositions of the present invention contain a sulfur-containing solvent, an aqueous liquid vehicle, and a colorant. The liquid vehicle can consist solely of water, or it can comprise a mixture of water and a water soluble or water miscible organic component, such as ethylene glycol, propylene glycol, diethylene glycols, glycerine, dipropylene glycols, polyethylene glycols, polypropylene glycols, amides, ethers, urea, substituted ureas, ethers, carboxylic acids and their salts, esters, alcohols, organosulfides, organosulfoxides, sulfones, alcohol derivatives, carbitol, butyl carbitol, cellusolve, tripropylene glycol monomethyl ether, ether derivatives, amino alcohols, ketones, N-methylpyrrolidinone, 2-pyrrolidinone, cyclohexylpyrrolidone, hydroxyethers, amides, sulfoxides, lactones, polyelectrolytes, methyl sulfonylethanol, imidazole, betaine, and other water soluble or water miscible materials, as well as mixtures thereof. When mixtures of water and water soluble or miscible organic liquids are selected as the liquid vehicle, the water to organic ratio typically ranges from about 100:0 to about 30:70, and preferably from about 97:3 to about 40:60. The non-water component of the liquid vehicle generally serves as a humectant which has a boiling point higher than that of water (100° C.). In the ink compositions of the present invention, the liquid vehicle is typically present in an amount of from about 80 to about 99.9 percent by weight of the ink, and preferably from about 90 to about 99 percent by weight of the ink, although the amount can be outside these ranges.

Ink compositions of the present invention also include a colorant. Dyes are suitable colorants for the inks of the present invention. Any suitable dye or mixture of dyes compatible with the ink liquid vehicle can be used, with water soluble anionic dyes and cationic dyes being preferred. Examples of suitable dyes include Food dyes such as Food Black No. 1, Food Black No. 2, Food Red No. 40, Food Blue No. 1, Food Yellow No. 7, and the like, FD & C dyes, Acid Black dyes (No. 1, 7, 9, 24, 26, 48, 52, 58, 60, 61, 63, 92, 107, 109, 118, 119, 131, 140, 155, 156, 172, 194, and the like), Acid Red dyes (No. 1, 8, 32, 35, 37, 52, 57, 92, 115, 119, 154, 249, 254, 256, and the like), Acid Blue dyes (No. 1, 7, 9, 25, 40, 45, 62, 78, 80, 92, 102, 104, 113, 117, 127, 158, 175, 183, 193, 209, and the like), Acid Yellow dyes (No. 3, 7, 17, 19, 23, 25, 29, 38, 42, 49, 59, 61, 72, 73, 114, 128, 151, and the like), Direct Black dyes (No. 4, 14, 17, 22, 27, 38, 51, 112, 117, 154, 168, and the like), Direct Blue dyes (No. 1, 6, 8, 14, 15, 25, 71, 76, 78, 80, 86, 90 106, 108, 123, 163, 165. 199, 226, and the like), Direct Red dyes (No. 1, 2, 16, 23, 24, 28, 39, 62, 72, 236, and the like), Direct Yellow dyes (No. 4, 11, 12, 27, 28, 33, 34, 39, 50, 58, 86, 100, 106, 107, 118, 127, 132, 142, 157, and the like), anthraquinone dyes, monoazo dyes, disazo dyes, phthalocyanine derivatives, including various phthalocyanine sulfonate salts, aza[18]annulenes, formazan copper complexes, triphenodioxazines, Bernacid Red 2BMN; Pontamine Brilliant Bond Blue A; Pontamine; Caro direct Turquoise FBL Supra Conc. (Direct Blue 199), available from Carolina Color and Chemical; Special Fast Turquoise 8GL Liquid (Direct Blue 86), available from Mobay Chemical; Intrabond Liquid Turquoise GLL (Direct Blue 86), available from Crompton and Knowles; Cibracron Brilliant Red 38-A (Reactive Red 4), available from Aldrich Chemical; Drimarene Brilliant Red X-2B (Reactive Red 56), available from Pylam, Inc.; Levafix Brilliant Red E-4B, available from Mobay Chemical; Levafix Brilliant Red E-6BA, available from Mobay Chemical; Procion Red H8B (Reactive Red 31), available from ICI America; Pylam Certified D&C Red #28 (Acid Red 92), available from Pylam; Direct Brilliant Pink B Ground Crude, available from Crompton & Knowles; Cartasol Yellow GTF Presscake, available from Sandoz, Inc.; Tartrazine Extra Conc. (FD&C Yellow #5, Acid Yellow 23), available from Sandoz; Carodirect Yellow RL (Direct Yellow 86), available from Carolina Color and Chemical; Cartasol Yellow GTF Liquid Special 110, available from Sandoz, Inc.; D&C Yellow #10 (Acid Yellow 3), available from Tricon; Yellow Shade 16948, available from Tricon, Basacid Black X34, available from BASF, Carta Black 2GT, available from Sandoz, Inc.; Neozapon Red 492 (BASF); Orasol Red G (Ciba-Geigy); Direct Brilliant Pink B (Crompton-Knolls); Aizen Spilon Red C-BH (Hodogaya Chemical Company); Kayanol Red 3BL (Nippon Kayaku Company); Levanol Brilliant Red 3BW (Mobay Chemical Company); Levaderm Lemon Yellow (Mobay Chemical Company); Spirit Fast Yellow 3G; Aizen Spilon Yellow C-GNH (Hodogaya Chemical Company); Sirius Supra Yellow GD 167; Cartasol Brilliant Yellow 4GF (Sandoz); Pergasol Yellow CGP (Ciba-Geigy); Orasol Black RL (Ciba-Geigy); Orasol Black RLP (Ciba-Geigy); Savinyl Black RLS (Sandoz); Dermacarbon 2GT (Sandoz); Pyrazol Black BG (ICI); Morfast Black Conc A (Morton-Thiokol); Diazol Black RN Quad (ICI); Orasol Blue GN (Ciba-Geigy); Savinyl Blue GLS (Sandoz); Luxol Blue MBSN (Morton-Thiokol); Sevron Blue 5GMF (ICI); Basacid Blue 750 (BASF); Bernacid Red, available from Berncolors, Poughkeepsie, NY; Pontamine Brilliant Bond Blue; Berncolor A.Y. 34; Telon Fast Yellow 4GL-175; BASF Basacid Black SE 0228; the Pro-Jet® series of dyes available from ICI, including Pro-Jet® Yellow I (Direct Yellow 86), Pro-Jet® Magenta I (Acid Red 249), Pro-Jet® Cyan I (Direct Blue 199), Pro-Jet® Black I (Direct Black 168), Pro-Jet® Yellow 1-G (Direct Yellow 132), Aminyl Brilliant Red F-B, available from Sumitomo Chemical Company (Japan), the Duasyn® line of "salt-free" dyes available from Hoechst, such as Duasyn® Direct Black HEF-SF (Direct Black 168), Duasyn® Black RL-SF (Reactive Black 31), Duasyn® Direct Yellow 6G-SF VP216 (Direct Yellow 157), Duasyn® Brilliant Yellow GL-SF VP220 (Reactive Yellow 37), Duasyn® Acid Yellow XX-SF LP413 (Acid Yellow 23), Duasyn® Brilliant Red F3B-SF VP218 (Reactive Red 180), Duasyn® Rhodamine B-SF VP353 (Acid Red 52), Duasyn® Direct Turquoise Blue FRL-SF VP368 (Direct Blue 199), Duasyn® Acid Blue AE-SF VP344 (Acid Blue 9), various Reactive dyes, including Reactive Black dyes, Reactive Blue dyes, Reactive Red dyes, Reactive Yellow dyes, and the like, as well as mixtures thereof. The dye is present in the ink composition in any effective amount, typically from about 0.5 to about 15 percent by weight, and preferably from about 1 to about 10 percent by weight, although the amount can be outside of these ranges.

Also suitable as a colorant are pigment particles. The pigment can be of any desired color, such as black, cyan, magenta, yellow, red, blue, green, brown, or the like, as well as mixtures thereof. Examples of suitable pigments include various carbon blacks such as channel black, furnace black, lamp black, Raven® 5250, Raven® 5750, Raven® 3500 and other similar carbon black products available from Columbia Company, Regal® 330, Black Pearl® L, Black Pearl® 1300, and other similar carbon black products available from Cabot Company, Degussa carbon blacks such as Color Black® series, Special Black® series, Printtex® series and Derussol® carbon black dispersions available from Degussa Company, Hostafine® series such as Hostafine® Yellow GR (Pigment 13), Hostafine® Yellow (Pigment 83), Hostafine® Red FRLL (Pigment Red 9), Hostafine® Rubine F6B (Pigment 184), Hostafine® Blue2G (Pigment Blue 15:3), Hostafine® Black T (Pigment Black 7), and Hostafine® Black TS (Pigment Black 7), available from Hoechst Celanese Corporation, Normandy Magenta RD-2400 (Paul Uhlich), Paliogen Violet 5100 (BASF), Paliogen Violet 5890 (BASF), Permanent Violet VT2645 (Paul Uhlich), Heliogen Green L8730 (BASF), Argyle Green XP-111-S (Paul Uhlich), Brilliant Green Toner GR 0991 (Paul Uhlich), Heliogen Blue L6900, L7020 (BASF), Heliogen Blue D6840, D7080 (BASF), Sudan Blue OS (BASF), PV Fast Blue B2G01 (American Hoechst), Irgalite Blue BCA (Ciba-Geigy), Paliogen Blue 6470 (BASF), Sudan III (Matheson, Coleman, Bell), Sudan II (Matheson, Coleman, Bell), Sudan IV (Matheson, Coleman, Bell), Sudan Orange G (Aldrich), Sudan Orange 220 (BASF), Paliogen Orange 3040 (BASF), Ortho Orange OR 2673 (Paul Uhlich), Paliogen Yellow 152, 1560 (BASF), Uithol Fast Yellow 0991K (BASF), Paliotol Yellow 1840 (BASF), Novoperm Yellow FG1 (Hoechst), Permanent Yellow YE 0305 (Paul Uhlich), Lumogen Yellow D0790 (BASF), Suco-Gelb L1250 (BASF), Suco-Yellow D1355 (BASF), Hostaperm Pink E (American Hoechst), Fanal Pink D4830 (BASF), Cinquasia Magenta (DuPont), Lithol Scarlet D3700 (BASF), Toluidine Red Aldrich), Scarlet for Thermoplast NSD PS PA (Ugine Kuhlmann of Canada), E. D. Toluidine Red (Aldrich), Uthol Rubine Toner (Paul Uhlich), Lithol Scarlet 4440 (BASF), Bon Red C (Dominion Color Company), Royal Brilliant Red RD-8192 (Paul Uhlich), Oracet Pink RF (Ciba-Geigy), Paliogen Red 3871K (BASF), Paliogen Red 3340 (BASF), and Uithol Fast Scarlet L4300 (BASF). Other pigments can also be selected. The pigment particles can be of any desired size. Typical average particle diameters for pigment particles in inks to be used in thermal ink jet printing processes, for example, are from about 0.001 to about 10 microns, preferably from about 0.01 to about 3 microns, and more preferably less than about 1 micron, although the average particle diameter can be outside these ranges. The pigment particles can be present in the ink in any desired amount. Typically the pigment particles are present in an amount of from about 1 to about 20 percent by weight, preferably from about 1 to about 10 percent by weight, more preferably from about 2 to about 8 percent by weight, and even more preferably from about 4 to about 7 percent by weight, although the amount can be outside these ranges.

Mixtures of one or more dyes and/or one or more pigments can also be employed for the colorant component of the inks of the present invention.

Other optional additives to the inks include biocides such as Dowicil 150, 200, and 75, benzoate salts, sorbate salts, and the like, present in an amount of from about 0.0001 to about 4 percent by weight of the ink, and preferably from about 0.01 to about 2.0 percent by weight of the ink, pH controlling agents such as acids or, bases, phosphate salts, carboxylates salts, sulfite salts, amine salts, and the like, present in an amount of from 0 to about 1 percent by weight of the ink and preferably from about 0.01 to about 1 percent by weight of the ink, or the like.

The ink compositions are generally of a viscosity suitable for use in thermal ink jet printing processes. At room temperature (i.e., about 25° C.), typically, the ink viscosity is no more than about 10 centipoise, and preferably is from about 1 to about 5 centipoise, more preferably from about 1 to about 4 centipoise, although the viscosity can be outside this range.

Ink compositions of the present invention can be of any suitable or desired pH. For some embodiments, such as thermal ink jet printing processes, typical pH values are from about 6.5 to about 9.25, and preferably from about 7 to about 8.75, although the pH can be outside of these ranges.

Ink compositions suitable for ink jet printing can be prepared by any suitable process. Typically, the inks are prepared by simple mixing of the ingredients. One process entails mixing all of the ink ingredients together and filtering the mixture to obtain an ink. Inks can be prepared by preparing a conventional ink composition according to any desired process, such as by mixing the ingredients, heating if desired, and filtering, followed by adding any desired additional additives to the mixture and mixing at room temperature with moderate shaking until a homogeneous mixture is obtained, typically from about 5 to about 10 minutes. Alternatively, the optional ink additives can be mixed with the other ink ingredients during the ink preparation process, which takes place according to any desired procedure, such as by mixing all the ingredients, heating if desired, and filtering.

The present invention is also directed to a process which entails incorporating an ink composition of the present invention into an ink jet printing apparatus and causing droplets of the ink composition to be ejected in an imagewise pattern onto a substrate. In one embodiment, the printing apparatus employs a thermal ink jet process wherein the ink in the nozzles is selectively heated in an imagewise pattern, thereby causing droplets of the ink to be ejected in imagewise pattern. In another embodiment, the printer employs an acoustic ink jet process, wherein droplets of the ink are caused to be ejected in imagewise pattern by acoustic beams. Any suitable substrate can be employed, including plain papers such as Xerox® 4024 papers, Xerox® Image Series papers, Courtland 4024 DP paper, ruled notebook paper, bond paper, silica coated papers such as Sharp Company silica coated paper, JuJo paper, and the like, transparency materials, fabrics, textile products, plastics, polymeric films, inorganic substrates such as metals and wood, and the like. In a preferred embodiment, the process entails printing onto a porous or ink absorbent substrate, such as plain paper.

Specific embodiments of the invention will now be described in detail. These examples are intended to be illustrative, and the invention is not limited to the materials, conditions, or process parameters set forth in these embodiments. All parts and percentages are by weight unless otherwise indicated.

EXAMPLE I

Anthium Dioxcide (preparation of $ClO_2$ stabilized in water, containing 5 percent by weight (50,000 parts per million) chlorine dioxide, 3.65 percent by weight buffering agents (sodium carbonates $Na_2CO_3$ and $NaHCO_3$), and 91.35 percent by weight water, obtained from International Dioxcide, Inc., Clark, N.J.) was diluted with water to bring the concentration to slightly above 2,000 ppm. The solution was then titrated with a 0.1 Normal HCl solution to a pH of about 3, as suggested by the manufacturer. The acid reacted with a sodium carbonate buffer, which is present in the commercial preparation to allow the effective $ClO_2$ concentration to be above the 3,000 ppm solubility limit. The final $ClO_2$ treatment solution contained 0.07 parts by weight Anthium Dioxcide, 27.64 parts by weight deionized water, and 2.29 parts by weight 0.1 N HCl. The technical literature on Anthium Dioxcide gives its pH as around 9.0. Before the acid titration, the dilution of 0.7 parts by weight Anthium Dioxcide with 26.8 parts by weight deionized water had a pH of 7.0 at 24.4° C. After titration with the acid, this solution (hereinafter referred to as the "$ClO_2$ treatment solution") had a pH of 3.14 at 24.4° C.

Sulfolane W (a liquid containing 97 percent by weight sulfolane and 3 percent by weight water) was obtained from Phillips 66. Bartlesville, Okla. Although purified to some extent, the sulfolane had a distinct, disagreeable odor and was unsuitable for use in inks to be used in a home or office environment.

The following solutions were then prepared:

| solution | parts by weight Sulfolane w | parts by weight ClO$_2$ treatment solution | ppm ClO$_2$ in solution | wt. % sulfolane in solution | weight ratio ClO$_2$ to sulfolane |
|---|---|---|---|---|---|
| 1 | 9.5 | 0.5 | 100 | 92.2 | 0.11 × 10$^{-3}$ |
| 2 | 9.5 | 1.25 | 232 | 85.7 | 0.26 × 10$^{-3}$ |
| 3 | 9.5 | 4.25 | 618 | 67.0 | 0.92 × 10$^{-3}$ |
| 4 | 9.5 | 9.5 | 1,000 | 48.5 | 2.1 × 10$^{-3}$ |
| control | (100%) | 0 | 0 | 100 | 0 |

Portions of each of the four solutions and the control were heated for about one hour in sealed containers in a 100° C. oven. When examined the following day, solutions 2, 3, and 4 had no odor, and solution 1 had a slight odor. The control remained unchanged and exhibited a significant odor. The odor evaluation process was repeated several weeks later with the same results.

For use in ink jet inks, it is preferred that no residual oxidant remain the deodorized solvent solution to prevent oxidation of other ink ingredients, such as dyes. Solutions 1 through 4 were tested for remaining oxidant using potassium iodide-starch test paper (Fisher Scientific). No color change was seen in any of the four solutions, indicating that no excess chlorine dioxide remained after the heat treatment.

EXAMPLE II 1 part by weight Anthium Dioxcide was mixed directly with 24 parts by weight Sulfolane W to make solution 5. There was no treatment of the Anthium Dioxcide with an acid solution prior to admixture with the Sulfolane W.

| solution | parts by weight Sulfolane w | parts by weight ClO$_2$ treatment solution | ppm ClO$_2$ in solution | wt. % sulfolane in solution | weight ratio ClO$_2$ to sulfolane |
|---|---|---|---|---|---|
| 5 | 24 | 1 | 2,000 | 93.1 | 2.1 × 10$^{-3}$ |

Solution 5 was heated as described in Example I. When examined the next day, solution 5 had no odor. Solution 5 was also tested for residual oxidant using potassium iodide-starch paper, with the result that no remaining oxidant was indicated.

EXAMPLE III

Hydrogen peroxide (stabilized, solution containing 50 percent by weight hydrogen peroxide in water, obtained from Fisher Scientific, Fair Lawn, N.J.) was mixed directly with Sulfolane W to make solution 6.

| solution | parts by weight Sulfolane W | parts by weight 50% H$_2$O$_2$ solution | ppm H$_2$O$_2$ in solution | wt. % sulfolane in solution | weight ratio H$_2$O$_2$ to sulfolane |
|---|---|---|---|---|---|
| 6 | 9.5 | 9.5 | 250,000 | 48.5 | 0.51 |

Solution 6 was heated as described in Example I. When examined the next day, solution 6 had no odor. Solution 6 was also tested for residual oxidant using potassium iodide-starch paper, with the result that remaining oxidant was indicated.

EXAMPLE IV

A 20,000 ppm hydrogen peroxide treatment solution was prepared by mixing 1.2 parts by weight of the 50 percent by weight H$_2$O$_2$ solution of Example III with 28.8 parts by weight deionized water. The following solutions were then prepared:

| solution | parts by weight Sulfolane W | parts by weight 20,000 ppm H$_2$O$_2$ solution | ppm H$_2$O$_2$ in solution | wt. % sulfolane in solution | weight ratio H$_2$O$_2$ to sulfolane |
|---|---|---|---|---|---|
| 7 | 9.5 | 0.5 | 1,000 | 92.2 | 1.1 × 10$^{-3}$ |
| 7 | 9.5 | 0.5 | 1,000 | 92.2 | 1.1 × 10$^{-3}$ |
| 8 | 9.5 | 1.25 | 2,326 | 85.7 | 2.7 × 10$^{-3}$ |
| 9 | 9.5 | 4.25 | 6,182 | 67.0 | 9.2 × 10$^{-3}$ |
| 10 | 9.5 | 9.5 | 10,000 | 48.5 | 20.6 × 10$^{-3}$ |

Solutions 7, 8, 9, and 10 were heated as described in Example I. When examined the next day, solutions 7, 8, 9, and 10 had no odor. Solutions 7, 8, 9, and 10 were also tested for residual oxidant using potassium iodide-starch paper, with the result that no remaining oxidant was indicated in any of the solutions.

EXAMPLE V

Ink compositions are prepared by admixing solutions 1 through 10 and the control, prepared as described in Examples I through IV, with other ink ingredients to form inks of the following composition:

| Ingredient | Supplier | Amount (wt. %) |
|---|---|---|
| PROJET YELLOW OAM dye (Acid Yellow 23)* | Zeneca Colors | 53.33 |
| sulfolane | — | 21 |
| tripropylene glycol monomethyl ether (DOWANOL TPM) | Dow Chemical Co. | 18 |
| DOWICIL 150/200 biocide | Dow Chemical Co. | 0.1 |
| polyethylene oxide** | Polysciences | 0.05 |
| urea | Aldrich Chemical Co. | 6 |
| N,N-bis(2-hydroxyethyl-2-amino-ethanesulfonic acid) | Aldrich Chemical Co. | 0.6 |

-continued

| Ingredient | Supplier | Amount (wt. %) |
|---|---|---|
| sodium hydroxide (20% by weight in water) | Aldrich Chemical Co. | 0.62 |

*solution containing 7.5% by weight dye solids in water
**bisphenol-A derivative, molecular weight 18,500, of the formula

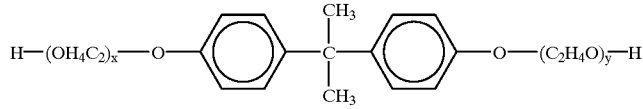

The inks are incorporated into a Xerox® XJ4C color thermal ink jet printer and used to jet images onto Xerox® Image Series LX paper under ambient office conditions. The inks are also incorporated into a Hewlett-Packard 1600C ink jet printer with the heater disabled and used to jet images onto Xerox® Image Series LX paper under ambient office conditions. It is believed that the inks containing sulfolane from solutions 2 through 10 will exhibit no undesirable odor; that the ink containing sulfolane from solution 1 will exhibit a slight odor; and that the ink containing the untreated sulfolane from the control will exhibit a significant odor, making it undesirable for use in a home or office environment.

EXAMPLE VI

Ink compositions are prepared by admixing solutions 1 through 10 and the control, prepared as described in Examples I through IV, with other ink ingredients to form inks of the following composition:

The inks are filtered through a 0.2 micron Gelman Nylaflow filter at 20 pounds per square inch. The inks are incorporated into a Xerox® XJ4C color thermal ink jet printer and used to jet images onto Xerox® Image Series LX paper under ambient lab conditions. The inks are also incorporated into a Hewlett-Packard 1600C ink jet printer with the heater disabled and used to jet images onto Xerox® Image Series LX paper under ambient office conditions. It is believed that the inks containing sulfolane from solutions 2 through 10 will exhibit no undesirable odor; that the ink containing sulfolane from solution 1 will exhibit a slight odor; and that the ink containing the untreated sulfolane from the control will exhibit a significant odor, making it undesirable for use in a home or office environment.

EXAMPLE VII

Ink compositions are prepared by admixing solutions 1 through 10 and the control, prepared as described in Examples I through IV, with other ink ingredients to form inks of the following composition:

| Ingredient | Supplier | Amount (grams) |
|---|---|---|
| deionized water | — | 755.5 |
| tris(hydroxymethyl) aminomethane | American Biorganics Inc. | 3 |
| ethylene diamine tetraacetic acid | Dow Chemical Co. | 2 |
| 261 RV cationic polymer | Calgon | 5 |
| DOWICIL 150/200 biocide | Dow Chemical Co. | 1 |
| polyethylene oxide* | Polysciences | 0.5 |
| sulfolane | — | 63 |
| urea | Aldrich Chemical Co. | 100 |
| lithium chloride | Aldrich Chemical Co. | 10 |
| TRITON X-100 surfactant | Aldrich Chemical Co. | 10 |
| PROJET RED OAM dye** | Zeneca Colors roll mill 30 minutes | 50 |

*bisphenol-A derivative, molecular weight 18,500, of the formula

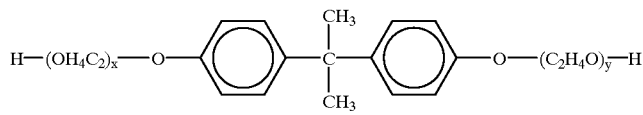

**solution containing 10% by weight dye solids in water

| Ingredient | Supplier | Amount (grams) |
|---|---|---|
| deionized water | — | 74.4 |
| tris(hydroxymethyl) aminomethane | American Biorganics Inc. | 1 |
| ethylene diamine tetraacetic acid | Dow Chemical Co. | 0.5 |
| lithium bromide | Aldrich Chemical Co. | 14 |
| sulfolane | — | 12.6 |
| polyethylene oxide* | Polysciences | 0.1 |
| DOWICIL 150/200 biocide | Dow Chemical Co. | 0.2 |
| urea | Aldrich Chemical Co. | 40 |
| VARIKEM 110** | Calgon | 30 |
| Direct Red 227 dye*** | Tricon Colors | 6 |
| BASACID BLACK X34 dye**** | BASF | 21.2 |
| | roll mill 30 minutes | |

*bisphenol-A derivative, molecular weight 18,500, of the formula

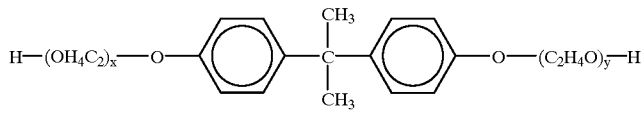

**aqueous solution containing 40 wt. % polymer in water
***aqueous solution containing 10 wt. % dye and 90 wt. % water
****aqueous solution containing 34 wt. % dye and 66 wt. % water The inks are incorporated into a Xerox® XJ4C color thermal ink jet printer and used to jet images onto Xerox® Image Series LX paper under ambient lab conditions. The inks are also incorporated into a Hewlett-Packard 1600C ink jet printer with the heater disabled and used to Jet images onto Xerox® Image Series LX paper under ambient office conditions. It is believed that the inks containing sulfolane from solutions 2 through 10 will exhibit no undesirable odor; that the ink containing sulfolane from solution 1 will exhibit a slight odor; and that the ink containing the untreated sulfolane from the control will exhibit a significant odor, making it undesirable for use in a home or office environment.

EXAMPLE VIII

Ink compositions are prepared by admixing solutions 1 through 10 and the control, prepared as described in Examples I through IV, with other ink ingredients to form inks of the following composition:

The resulting inks are filtered through a 1.2 micron Memtec filter at 20 pounds per square inch. The inks are incorporated into a Xerox® XJ4C color thermal ink jet printer and used to jet images onto Xerox® Image Series LX paper under ambient lab conditions. The inks are also incorporated into a Hewlett-Packard 1600C ink jet printer with the heater disabled and used to jet images onto Xerox® Image Series LX paper under ambient office conditions. It is believed that the inks containing sulfolane from solutions 2 through 10 will exhibit no undesirable odor; that the ink containing sulfolane from solution 1 will exhibit a slight odor; and that the ink containing the untreated sulfolane from the control will exhibit a significant odor, making it undesirable for use in a home or office environment.

Other embodiments and modifications of the present invention may occur to those of ordinary skill in the art subsequent to a review of the information presented herein; these embodiments and modifications, as well as equivalents thereof, are also included within the scope of this invention.

| Ingredient | Supplier | Amount (grams) |
|---|---|---|
| deionized water | — | 1059.8 |
| DOWICIL 150/200 biocide | Dow Chemical Co. | 4 |
| polyethylene oxide* | Polysciences | 2 |
| imidazole | American Biorganics | 40 |
| ethylene diamine tetraacetic acid | Dow Chemical Co. | 2.6 |
| sulfolane | — | 600 |
| acetylethanolamine** | Scher Chemical | 640 |
| butyl carbitol | Van Waters & Rogers | 480 |
| PROJET CYAN 1 dye*** | Zeneca Colors | 600 |
| PROJET BLUE OAM (Acid Blue 9) dye**** | Zeneca Colors | 571.6 |
| | roll mill 30 minutes | |

*bisphenol-A derivative, molecular weight 18,500, of the formula

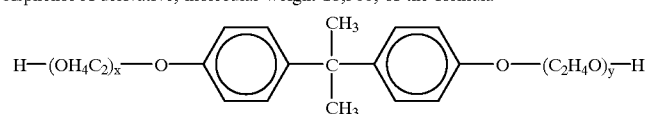

**aqueous solution containing 75 wt. % acetylethanolamine and 25 wt. % water
***aqueous solution containing 10 wt. % dye solids and 90 wt. % water
****aqueous solution containing 10 wt. % dye solids and 90 wt. % water

What is claimed is:

1. A process which comprises contacting a sulfur-containing solvent with an oxidizing agent, said sulfur-containing solvent containing odor-causing impurities, thereby oxidizing said impurities and reducing odor.

2. A process according to claim 1 wherein subsequent to contacting the sulfur-containing solvent with the oxidizing agent, the oxidizing agent is either removed from the sulfur-containing solvent or converted to a non-oxidizing compound.

3. A process according to claim 1 wherein the oxidizing agent is selected from the group consisting of chlorine dioxide, hydrogen peroxide, alkali metal peroxides, alkaline earth metal peroxides, alkyl hydroperoxides, dialkyl peroxides, acyl peroxides, peroxydisulfates, peroxyborates, percarbonates, and mixtures thereof.

4. A process according to claim 1 wherein the oxidizing agent is chlorine dioxide.

5. A process according to claim 1 wherein the sulfur-containing solvent is selected from the group consisting of 2,4-dimethylsulfolane, 3-methylsulfolane, dimethyl sulfoxide, and mixtures thereof.

6. A process which comprises contacting a sulfur-containing solvent with an oxidizing agent, said sulfur-containing solvent containing odor-causing impurities, thereby reducing odor, wherein the sulfur-containing solvent is sulfolane.

7. A process according to claim 6 wherein the oxidizing agent is chlorine dioxide.

8. A process according to claim 1 wherein the ratio by weight of oxidizing agent to sulfur-containing solvent is from about $1 \times 10^{-5}:1$ to about $1 \times 10^{-2}:1$.

9. A process according to claim 1 wherein the oxidizing agent is admixed with the sulfur-containing solvent.

10. A process which comprises contacting a sulfur-containing solvent with an oxidizing agent, said sulfur-containing solvent containing odor-causing impurities, thereby reducing odor, wherein the sulfur-containing solvent is passed through a solid material comprising either (a) a solid oxidizing agent, or (b) a solid material onto the surface of which is adsorbed an oxidizing agent.

11. A process for preparing an ink composition which comprises: (a) contacting a sulfur-containing solvent with an oxidizing agent, said sulfur-containing solvent containing odor-causing impurities, thereby oxidizing said impurities and reducing odor; and (b) admixing the sulfur-containing solvent with water and a colorant, thereby forming an ink composition.

12. A process according to claim 11 wherein subsequent to contacting the sulfur-containing solvent with the oxidizing agent, the oxidizing agent is either removed from the sulfur-containing solvent or converted to a non-oxidizing compound.

13. A process according to claim 11 wherein the oxidizing agent is selected from the group consisting of chlorine dioxide, hydrogen peroxide, alkali metal peroxides, alkaline earth metal peroxides, alkyl hydroperoxides, dialkyl peroxides, acyl peroxides, peroxydisulfates, peroxyborates, percarbonates, and mixtures thereof.

14. A process according to claim 11 wherein the oxidizing agent is chlorine dioxide.

15. A process according to claim 11 wherein the sulfur-containing solvent is selected from the group consisting of 2,4-dimethylsulfolane, 3-methylsulfolane, dimethyl sulfoxide, and mixtures thereof.

16. A process for preparing an ink composition which comprises: (a) contacting a sulfur-containing solvent with an oxidizing agent, said sulfur-containing solvent containing odor-causing impurities, thereby reducing odor; and (b) admixing the sulfur-containing solvent with water and a colorant, thereby forming an ink composition, wherein the sulfur-containing solvent is sulfolane.

17. A process according to claim 16 wherein the oxidizing agent is chlorine dioxide.

18. A process according to claim 11 wherein the ratio by weight of oxidizing agent to sulfur-containing solvent is from about $1 \times 10^{-5}:1$ to about $1 \times 10^{-2}:1$.

19. A process according to claim 11 wherein the oxidizing agent is admixed with the sulfur-containing solvent.

20. A process for preparing an ink composition which comprises: (a) contacting a sulfur-containing solvent with an oxidizing agent, said sulfur-containing solvent containing odor-causing impurities, thereby reducing odor, and (b) admixing the sulfur-containing solvent with water and a colorant, thereby forming an ink composition, wherein the sulfur-containing solvent is passed through a solid material comprising either (a) a solid oxidizing agent, or (b) a solid material onto the surface of which is adsorbed an oxidizing agent.

21. A process according to claim 11 which further comprises incorporating the ink composition thus prepared into an ink jet printing apparatus and causing droplets of the ink composition to be ejected in an imagewise pattern onto a substrate.

22. A process according to claim 21 wherein the printing apparatus employs a thermal ink jet process wherein the ink in the nozzles is selectively heated in an imagewise pattern, thereby causing droplets of the ink to be ejected in imagewise pattern.

23. A process for preparing an ink composition which comprises: (a) contacting a sulfur-containing solvent with an oxidizing agent, said sulfur-containing solvent containing odor-causing impurities, thereby reducing odor; and (b) admixing the sulfur-containing solvent with water and a colorant, thereby forming an ink composition, said process further comprising incorporating the ink composition thus prepared into an inkjet printing apparatus and causing droplets of the ink composition to be ejected in an imagewise pattern onto a substrate, wherein the printer employs an acoustic ink jet process, wherein droplets of the ink are caused to be ejected in imagewise pattern by acoustic beams.

24. A process according to claim 1 wherein the sulfur-containing solvent is selected from the group consisting of 2,4-dimethylsulfolane, 3-methylsulfolane, and mixtures thereof.

* * * * *